US009227855B2

(12) United States Patent
Basu et al.

(10) Patent No.: US 9,227,855 B2
(45) Date of Patent: Jan. 5, 2016

(54) LARGE-SCALE ELECTRICITY-LESS DISINFECTION OF FLUENT WATER

(71) Applicant: International Business Machines Corporation, Armonk, NY (US)

(72) Inventors: Anirban Basu, Elmsford, NY (US); Stephen W. Bedell, Wappingers Falls, NY (US); Wilfried E. Haensch, Somers, NY (US); Davood Shahrjerdi, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 367 days.

(21) Appl. No.: 13/756,734

(22) Filed: Feb. 1, 2013

(65) Prior Publication Data
US 2014/0131286 A1 May 15, 2014

Related U.S. Application Data

(63) Continuation-in-part of application No. 13/673,520, filed on Nov. 9, 2012.

(51) Int. Cl.
*C02F 1/32* (2006.01)
*A61L 9/00* (2006.01)
*A61L 2/00* (2006.01)

(52) U.S. Cl.
CPC . *C02F 1/325* (2013.01); *A61L 2/00* (2013.01); *A61L 9/00* (2013.01); *C02F 2201/009* (2013.01);
(Continued)

(58) Field of Classification Search
CPC ........ C02F 1/30; C02F 1/32; C02F 2201/009; C02F 2209/40; C02F 2209/11; C02F 2303/04; A61L 9/00; A61L 2/00
USPC ........... 210/739, 748.01, 748.11, 87, 91, 105, 210/192, 242.1, 295, 799; 422/24, 186, 422/186.3, 400; 136/243, 244, 252, 261
See application file for complete search history.

(56) References Cited

U.S. PATENT DOCUMENTS 4,438,337 A * 3/1984 Forrat ........................... 250/436
4,740,431 A * 4/1988 Little ............................... 429/9
(Continued)

FOREIGN PATENT DOCUMENTS

WO  WO 2008033016 A1 * 3/2008
WO  WO 2009-108045 A1   9/2009

OTHER PUBLICATIONS

Daniel Mausezah et al., "Solar Drinking Water Disinfection (SODIS) to Reduce Childhood Diarrhoea in Rural Bolivia: A Cluster-Randomized, Controlled Trial", 2009.
(Continued)

*Primary Examiner* — Walter D Griffin
*Assistant Examiner* — Cameron J Allen
(74) *Attorney, Agent, or Firm* — Louis Percello

(57) ABSTRACT

A system for disinfecting a water sample includes a pipe having an inlet for engaging a source of the water sample, a storage reservoir connected to an outlet of the pipe for holding the water sample, an array of photovoltaic cells coupled to the pipe for converting solar radiation into a current, and an array of light emitting diodes coupled to the pipe and powered by the current, wherein the array of light emitting diodes emits a germicidal wavelength of radiation. A method for disinfecting a fluent water sample includes generating a current using an array of photovoltaic cells, using the current to power an array of light emitting diodes, wherein the array of light emitting diodes emits a germicidal wavelength of radiation, and exposing the fluent water sample to the radiation while transporting the fluent water sample from a source to a storage reservoir.

20 Claims, 4 Drawing Sheets

(52) U.S. Cl.
CPC . *C02F 2201/3222* (2013.01); *C02F 2201/3227* (2013.01); *C02F 2209/11* (2013.01); *C02F 2209/36* (2013.01); *C02F 2209/40* (2013.01); *C02F 2303/04* (2013.01)

(56) References Cited

U.S. PATENT DOCUMENTS

| | | | |
|---|---|---|---|
| 5,013,417 A * | 5/1991 | Judd, Jr. | 204/229.5 |
| 6,299,770 B1 * | 10/2001 | Diener et al. | 210/252 |
| 8,507,941 B2 | 8/2013 | Khan et al. | |
| 2005/0242013 A1 * | 11/2005 | Hunter et al. | 210/143 |
| 2005/0258108 A1 | 11/2005 | Sanford | |
| 2006/0131246 A1 | 6/2006 | Ehlers, Sr. | |
| 2006/0131511 A1 | 6/2006 | Ehlers, Sr. | |
| 2006/0163126 A1 * | 7/2006 | Maiden | 210/87 |
| 2007/0003430 A1 * | 1/2007 | Kaiser et al. | 422/24 |
| 2007/0181508 A1 | 8/2007 | Gui et al. | |
| 2008/0035581 A1 | 2/2008 | Kuhlmann et al. | |
| 2009/0084734 A1 | 4/2009 | Yencho et al. | |
| 2010/0155339 A1 | 6/2010 | Gunter et al. | |
| 2010/0311250 A1 | 12/2010 | Bedell et al. | |
| 2011/0210268 A1 | 9/2011 | Dornseifer et al. | |
| 2011/0214709 A1 | 9/2011 | Evelsizer et al. | |

OTHER PUBLICATIONS

Yoon, et al., "Ultrathin Silicon Solar Microcells for Semitransparent, Mechanically Flexible and Microconcentrator Module Designs". Nature Materials, vol. 7. Nov. 2008.

\* cited by examiner

US 9,227,855 B2

LARGE-SCALE ELECTRICITY-LESS DISINFECTION OF FLUENT WATER

CROSS REFERENCE TO RELATED APPLICATIONS

This application is a continuation-in-part of co-pending U.S. patent application Ser. No. 13/673,520, filed Nov. 9, 2012, which is herein incorporated by reference in its entirety.

FIELD OF THE DISCLOSURE

The present disclosure relates generally to water disinfection and relates more specifically to large-scale electricity-less water disinfection systems.

BACKGROUND OF THE DISCLOSURE

Recent studies by the World Health Organization indicate that as many as one billion people lack access to a source of improved drinking water. Consequently, more than two million people die per year of waterborne disease, and more still are afflicted with non-fatal waterborne diseases. Most of these people live in developing countries, refugee camps, or disaster relief shelters, where conventional water treatment systems may be cost-prohibitive (or the resources required to power such systems—e.g., electricity, fuel, etc.—may not be readily available).

Conventional approaches to electricity-less water disinfection include of ultraviolet (UV) germicidal irradiation, which typically uses a mercury vapor lamp to deliver germicidal UV radiation. Although such systems compare favorably with other water disinfection systems, they also introduce environmental hazards that other systems do not. For instance, a full-spectrum mercury vapor lamp will produce ozone at certain wavelengths. Moreover, exposure to germicidal wavelengths of UV radiation can be harmful to humans (e.g., resulting in sunburn, skin cancer, or vision impairment).

SUMMARY OF THE DISCLOSURE

A system for disinfecting a water sample includes a pipe having an inlet for engaging a source of the water sample, a storage reservoir connected to an outlet of the pipe for holding the water sample, an array of photovoltaic cells coupled to the pipe for converting solar radiation into a current, and an array of light emitting diodes coupled to the pipe and powered by the current, wherein the array of light emitting diodes emits a germicidal wavelength of radiation.

A method for disinfecting a fluent water sample includes generating a current using an array of photovoltaic cells, using the current to power an array of light emitting diodes, wherein the array of light emitting diodes emits a germicidal wavelength of radiation, and exposing the fluent water sample to the radiation while transporting the fluent water sample from a source to a storage reservoir.

BRIEF DESCRIPTION OF THE DRAWINGS

The teachings of the present disclosure can be readily understood by considering the following detailed description in conjunction with the accompanying drawings, in which.

To facilitate understanding, identical reference numerals have been used, where possible, to designate identical elements that are common to the Figures.

DETAILED DESCRIPTION

In one embodiment, the present invention is a method and apparatus for large-scale electricity-less disinfection of fluent water. Within the context of the present invention, "electricity-less" is understood to refer to the absence of a conventional infrastructure for delivering electricity (e.g., a power distribution grid). However, as will become apparent, embodiments of the present invention employ mechanisms for converting renewable sources of energy into direct current electricity. In particular, embodiments of the present invention disinfect water using an array of light emitting diodes (LEDs) powered by photovoltaic cells, thereby obviating the need for a conventional source of electricity. The water is efficiently and effectively disinfected while being flowed to a storage reservoir using a system that is more compact, consumes less power, and is safer environmentally than conventional disinfection systems.

Figure 1:
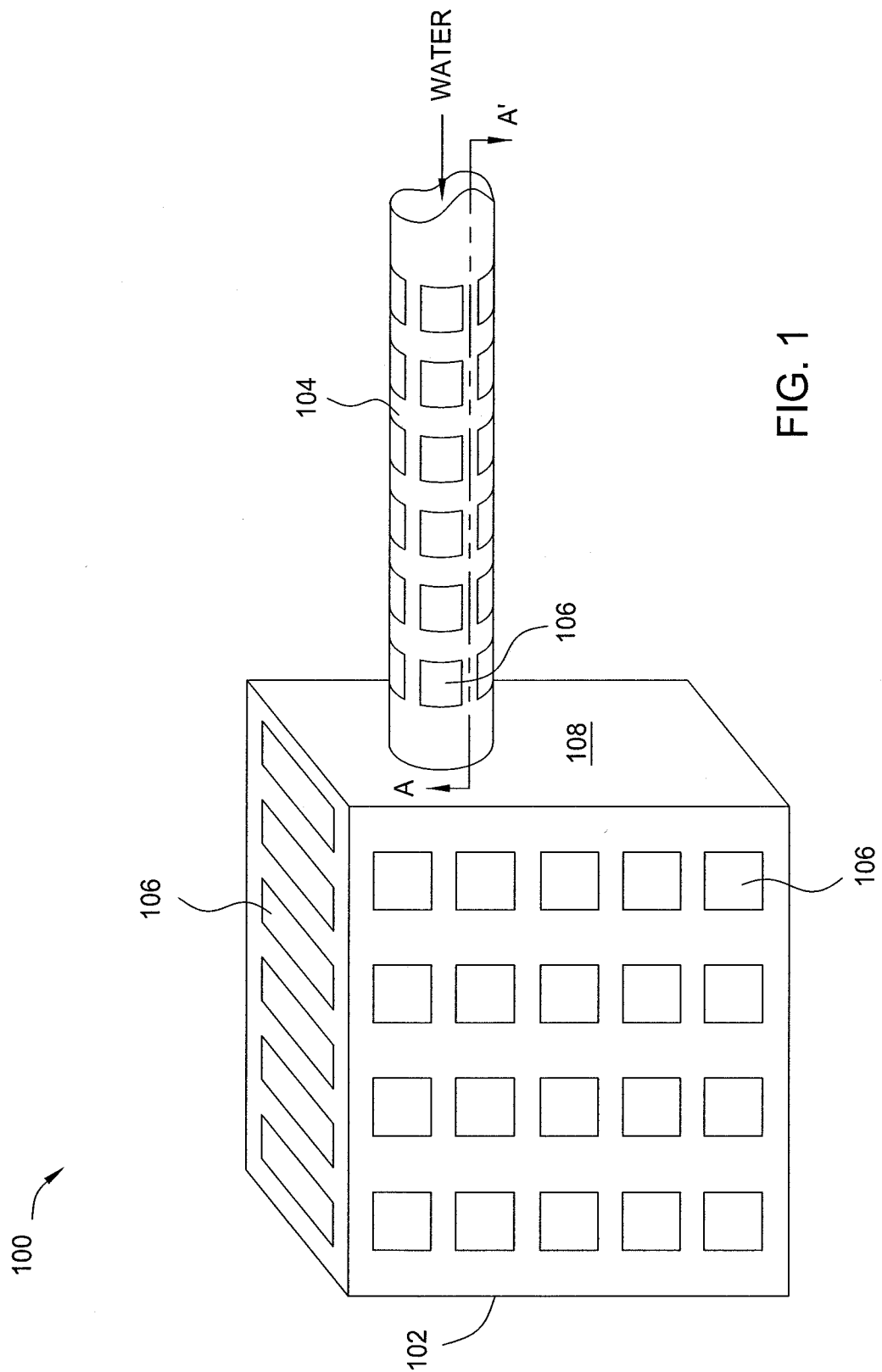
FIG. 1 is a plan view illustrating one embodiment of a water disinfection system, according to the present invention.
Figure 2:
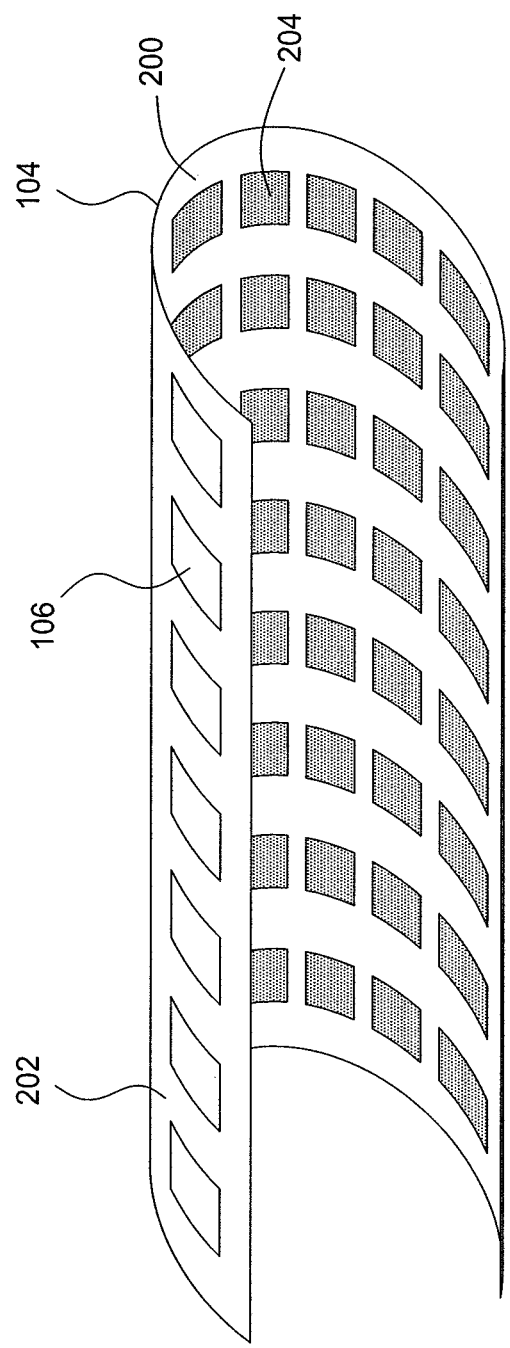
FIG. 2 is a cross-sectional view of a portion of the water disinfection system illustrated in FIG. 1, taken along line A-A' of FIG. 1.

FIG. 1 is a plan view illustrating one embodiment of a water disinfection system 100, according to the present invention. FIG. 2 is a cross-sectional view of a portion of the water disinfection system 100 illustrated in FIG. 1, taken along line A-A' of FIG. 1. The water disinfection system 100 employs a chemical-free process that directly attacks the vital deoxyribonucleic acid (DNA) of microorganisms (e.g., bacteria, mold, yeast, viruses, protozoa, etc.) in a water sample, thereby sterilizing the microorganisms and rendering the water sample suitable for human consumption.

Referring simultaneously to FIGS. 1 and 2, the system 100 generally comprises a storage reservoir 102 connected to a first end (i.e., an inlet) of a pipe 104. A second end (i.e., an outlet) of the pipe 102 is connected to or is otherwise in contact with a water source (not shown). Thus, the pipe 104 is operable to convey water (which is not necessarily disinfected) from the water source to the storage reservoir 102. Some embodiments of the system 100 may require additional components to mechanically move the water through the pipe 104 (e.g., a pump). In one embodiment, at least the pipe 104 is positioned in a location where it will be exposed to radiation (e.g., sunlight).

Referring simultaneously to FIGS. 1 and 2, the pipe 104 comprises a hollow body having an interior wall 200 and an exterior wall 202. The hollow body may take the shape or a cylinder or another shape. The pipe 104 thus defines a volume within which a quantity of water can be transported and disinfected according to the embodiments described below. In one embodiment, the pipe 104 is formed from a material that is known to be environmentally and health-safe (i.e., does not cause any significant negative environmental or health-related side effects), such as a Bisphenol A (BPA)-free polymer or plastic. In one embodiment, the pipe 104 includes a sensor (e.g., a photodiode based sensor) at either or both of its first end and second end. The sensors are positioned to detect turbidity and/or obstructions at the inlet and/or outlet of the pipe 104. Detection of turbidity and/or obstructions allows the system 100 to be shut down for responsive maintenance or repairs, so that the system can continue to provide sufficiently disinfected water.

The storage reservoir 102 comprises a container defining an interior volume that holds a quantity of water transported by the pipe 104. Although the storage reservoir 102 in FIG. 1 is illustrated as being substantially cube-shaped, the storage container 102 may be formed in a variety of shapes and sizes. In a further embodiment, the storage reservoir 102 includes one or more biosensors that monitor the level of water disinfection and ensure that the water is safe for human consumption.

The system 100 further comprises a plurality of arrays of photovoltaic cells 106 (i.e., semiconductors that convert solar radiation to direct current electricity). In one embodiment, the photovoltaic cells 106 are coupled to the exterior wall 202 of the pipe 104, as well as to at least a portion of an exterior surface 108 of the storage reservoir 102. In one embodiment, an array of photovoltaic cells 106 encircles an entire perimeter of the pipe's exterior wall 202. In one embodiment, the photovoltaic cells 106 comprise micro-photovoltaic cells (e.g., photovoltaic cells having a size between approximately ten and one hundred micron). In a further embodiment, the photovoltaic cells 106 are spalled (i.e., thin-film), flexible photovoltaic cells. For instance, the thickness of the photovoltaic cells 106 may be between approximately fifteen and forty micron and have a bending radius of approximately five millimeters. The photovoltaic cells 106 may also be substantially transparent; the exact degree of transparency is a user-definable design parameter (as an example, the photovoltaic cells 106 may be approximately seventy percent transparent). In one embodiment, one or more of the photovoltaic cells 106 is formed from at least one of: amorphous silicon, crystalline silicon, silicon germanium (SiGe), germanium (Ge), indium gallium arsenide (InGaAs), or indium arsenide (InAs). Although the photovoltaic cells 106 in FIGS. 1 and 2 are illustrated as have rectangular dimensions, the photovoltaic cells 106 may be formed in a variety of shapes and sizes.

In a further embodiment, the photovoltaic cells 106 include a backup power source, such as an integrated thin-film battery or a connected external battery module. The backup power source stores electricity when the photovoltaic cells 106 are exposed to radiation, so that electricity is available even when a sufficient source of radiation is not immediately available.

In addition, an array of LEDs 204 is coupled to the interior wall 200 of the pipe 104. In one embodiment, the array of LEDs 204 encircles an entire perimeter of the interior wall 200. The array of LEDs 204 is also connected (e.g., by a system of interconnects) to the array of photovoltaic cells 106 on the pipe's exterior wall 202 and/or to the arrays of photovoltaic cells 106 on the outer surface 108 of the storage reservoir 102 such that current can pass from the photovoltaic cells 106 to the LEDs 204. In one embodiment, the LEDS 204 comprise micro-LEDs (e.g., LEDs having dimensions less than or equal to one hundred micrometers×one hundred micrometers). In a further embodiment, the LEDs 204 are spalled, flexible micro-LEDs arranged on a substrate (e.g., a silicon substrate) and coupled via a system of interconnects. For instance, the thickness of the LEDs 204 may be between approximately 4.8 and 5 micron. In one embodiment, the micro LEDs are formed from aluminum gallium nitride (AlGaN) and/or gallium nitride (GaN). In one embodiment, each of the LEDs 204 has a power output of approximately one milliwatt. In one embodiment, the array of LEDs 204 includes a plurality of different types of LEDs that collectively emit a range of wavelengths of germicidal radiation (e.g., 265 to 280 nanometers).

In a further embodiment, arrays of LEDs similar to the LEDs 204 may also be coupled to one or more of the interior surfaces of the storage reservoir 102. This will allow the water to be further disinfected in the storage reservoir 102; however, it will also increase the manufacturing costs of the system 100.

The system 100 has been demonstrated to be capable of sterilizing up to at least ninety-nine percent of many different types of microorganisms in water. Water that has been sterilized to this degree would generally be considered potable.

As discussed above, photovoltaic cells 106 are used to power the LEDs 204. The efficiency of inverted metamorphic III-V solar cells has been shown to be greater than thirty-six percent at one kilowatt per square meter, which corresponds to thirty-six milliwatts per square centimeter. For an exemplary array one hundred by one hundred micro LEDs having power outputs of one milliwatt, a power supply of ten watts is needed. Thus, based on the demonstrated efficiency of the solar cells discussed above, a one hundred square centime area of solar cells can provide 3600 milliwatts, or 3.6 watts. Therefore, a net area of three hundred square centimeters of solar cells would be sufficient to power an array of ten thousand micro LEDs.

Figure 3:
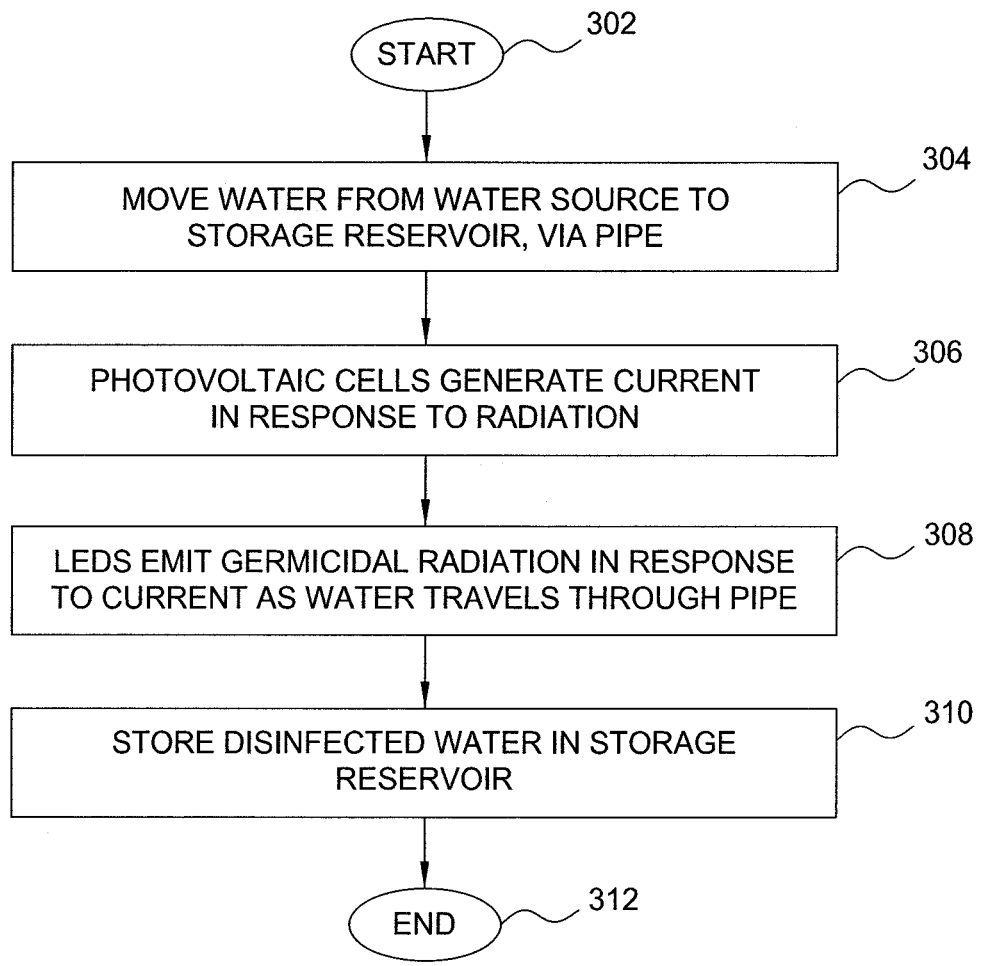
FIG. 3 is a flow diagram illustrating one embodiment of a method for disinfecting and transporting water, according to the present invention.

FIG. 3 is a flow diagram illustrating one embodiment of a method 300 for disinfecting and transporting water, according to the present invention. In particular, FIG. 3 illustrates how fluent water may be disinfected using the water disinfection system 100 illustrated in FIGS. 1 and 2. As such, reference is made in the discussion of the method 300 to various items illustrated in FIGS. 1 and 2.

The method 300 begins in step 302. In step 304, water from the water source is transported through the pipe 104, moving toward the storage reservoir 102. In one embodiment, the flow rate of the water through the pipe 104 is approximately one and a half to three centimeters per second.

In step 306, the array 104 of photovoltaic cells 106 on the exterior wall 202 of the pipe 104 and/or the arrays of photovoltaic cells 106 on the exterior surface 108 of the storage reservoir 102 generates a current in response to radiation to which the pipe 104 and/or storage reservoir is or has been exposed. In one embodiment, the arrays of photovoltaic cells 106 store the current using a backup power source (e.g., an integrated thin-film battery or an external battery module). In one embodiment, the current generated by the photovoltaic cells 106 is in the milliwatt range.

In step 308, the array of LEDs 204 on the interior wall 200 of the pipe 104 is powered and emits germicidal radiation in response to the current provided by the photovoltaic cells 106. In one embodiment, the array of LEDs 204 is powered directly by the photovoltaic cells 106 (i.e., using current that has been generated from radiation in substantially real time). In another embodiment, the array of LEDs 204 is powered by the backup power source that stores current previously generated by the LEDs 204. Thus, the array of LEDs 204 can be powered when radiation is immediately available (e.g., during the day) or when only stored electricity is available (e.g., at night). In one embodiment, the germicidal radiation is UV radiation (e.g., having a wavelength in the range of approximately 265 to 280 nanometers). Prolonged exposure to this germicidal radiation results in the sterilization of microorganisms in the water as it travels through the pipe 104. As a result, the water is disinfected and rendered suitable for human consumption. In one embodiment, the length of time for which the water must be exposed to the germicidal radiation depends at least on flow rate of the water through the pipe 104, the desired percentage and type of microorganisms to be sterilized, and the intensity of the germicidal radiation emitted by the LEDs 204. Disinfection of the water is thus a product of the intensity of the germicidal radiation emitted by the LEDs 204 over the time of exposure and within the given area (i.e., the volume of the pipe 104). This exposure may be expressed in microwatt seconds per square centimeter. In particular, the light intensity at a distance r from the LEDs 204 may be expressed as:

$$I(r)=Io/(4\pi r^2) \qquad \text{(EQN. 1)}$$

where I(r) is the light intensity at the distance r from the LED source, and Io is the light intensity at the LED source (i.e., r=0).

The diameter and length of the pipe 104 will determine the flow rate that is necessary to be germicidally effective for a given size and spacing of LEDs 204; thus, the design parameters are the length and diameter of the pipe 104, LED intensity, and LED spacing (one or more of these design parameters may be modified for optimal performance). Using EQN. 1 and assuming certain spacing between the LEDs 204, the flow rate and pipe dimensions can be estimated based on a reverse engineered calculation of the LED light intensity that is considered germicidally effective for the entire volume of water. As a specific example, the pipe 104 may have a length of thirty centimeters and a radius of fifteen centimeters. The LEDs 204 may have dimensions of one hundred micrometers×one hundred micrometers and power outputs of one milliwatt, and the horizontal and vertical spacing between each pair of LEDs 204 may be one centimeter. In this case, the average intensity of the exposure of the water to the germicidal radiation would be 0.683 milliwatts per square centimeter. Assuming an exposure time of twenty seconds, the total germicidal energy produced would thus be 13.65 milliwatts per square centimeter.

If the radius of the pipe is reduced to ten centimeters, the average intensity of the exposure of the water to the germicidal radiation would be 1.245 milliwatts per square centimeter. Assuming an exposure time of twenty seconds, the total germicidal energy produced would thus be 24.9 milliwatts per square centimeter. Assuming instead an exposure time of ten seconds, the total germicidal energy produced would thus be 12.45 milliwatts per square centimeter.

In step 310, the disinfected water is stored in the storage reservoir 102.

The method 300 ends in step 312.

The method 300 thus employs a physical, chemical-free process that effectively and efficiently disinfects water as it is transported for storage, without consuming electricity or causing any significant environmental side effects. Because the system 100 is compact and does not require electricity or fuel other than sunlight, it can be used in substantially any environment.

Moreover, the system 100 is cost effective to manufacture and to use. In particular, certain techniques, such as spalling, may be used to manufacture the system 100 in a manner that minimizes waste of materials or energy.

Figure 4:
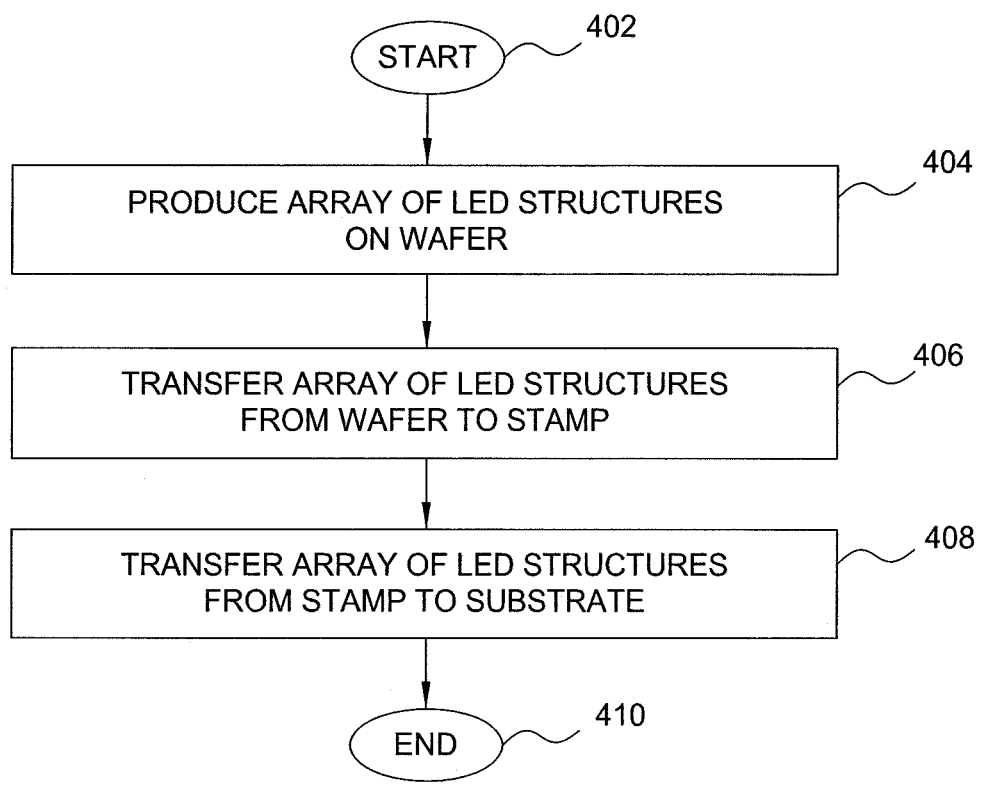
FIG. 4 is a flow diagram illustrating one embodiment of a method for manufacturing the water disinfection system illustrated in FIGS. 1 and 2.

FIG. 4 is a flow diagram illustrating one embodiment of a method 400 for manufacturing the water disinfection system 100 illustrated in FIGS. 1 and 2. In particular, the method 400 is one embodiment of a method for producing an array of LEDs 204 on the interior wall 200 of the pipe 204. The particular method 400 illustrated in FIG. 4 relies on a spalling technique to produce the array of LEDs 204.

The method 400 begins in step 402. In step 404, an array of LED structures is produced on a wafer (e.g., a silicon substrate). The array of LED structures may be produced using any one or more known manufacturing techniques. For instance, a stack of layers comprising a silicon substrate, an aluminum nitride layer formed on the silicon substrate, and a gallium nitride layer formed on the aluminum nitride layer can be fabricated. The stack may additionally comprise a plurality of contacts (e.g., p- and n-type contacts). Dry etching of the aluminum nitride and gallium nitride layers can expose the silicon substrate, which may then be anisotropically etched using potassium hydroxide (KOH), leaving an array of anchored gallium nitride/aluminum nitride structures.

In step 406, the array of LED structures is transferred from the wafer to a stamp. For instance, a patterned polydimethylsiloxane (PDMS) stamp may be brought into contact with the wafer and then quickly removed, causing chips of gallium nitride/aluminum nitride to be released from the wafer and adhered to the stamp as a plurality of discrete thin film devices. This technique may also be referred to as "spalling."

In step 408, the array of LED structures is transferred from the stamp to a substrate. For instance, the stamp may be brought into contact with the substrate and then slowly removed, causing the array of LED structures to adhere to the substrate as a plurality of discrete thin film devices (i.e., the array of LEDs). This may be accomplished using a transfer printing technique. In one embodiment, the substrate already includes a layer of interconnects (and adhesive) onto which the thin film devices are deposited. An additional layer of interconnects may then be deposited on the thin film devices (e.g., after planarization of the thin film devices). As a result, a printed array of micro LEDs is fabricated upon the substrate. In one embodiment, the substrate is or will become the inner wall 200 of the pipe 104. Thus, in one embodiment, the substrate is a BPA-free polymer.

The method 400 ends in step 410.

The method 400 thus results in the application of an array of thin-film LEDs 204 to the inner wall 200 of the pipe 104. As discussed above, spalling can also be used to apply an array of photovoltaic cells 106 to the outer surface 108 of the storage reservoir 102 or the outer wall 202 of the pipe 104. This technique allows a dense array to be distributed on a sparse array, thereby making economical use of materials by reducing the cost and area of material used. The photovoltaic cells and/or LEDs formed by this technique are flexible; however the precise degree of flexibility is not typically a design concern when the LEDs are manufactured on the micrometer scale as described above (since the LEDs individually occupy negligible real estate on the surface to which they are adhered).

Although various embodiments which incorporate the teachings of the present invention have been shown and described in detail herein, those skilled in the art can readily devise many other varied embodiments that still incorporate these teachings.

What is claimed is:

1. A system for disinfecting a sample of water, the system comprising:
a pipe having an inlet for engaging a source of the sample of water;
a storage reservoir connected to an outlet of the pipe for holding the sample of water;
a first array of photovoltaic cells coupled to an exterior wall of the pipe for converting solar radiation into a current, wherein the array of photovoltaic cells encircles the exterior wall of the pipe, wherein the array of photovoltaic cells comprises a plurality of micro photovoltaic cells, wherein the plurality of micro photovoltaic cells includes flexible thin-film photovoltaic cells; and
an array of flexible light emitting diodes coupled directly to an interior wall of the pipe and powered by the current, wherein the array of flexible light emitting diodes emits a germicidal wavelength of radiation, wherein the array of flexible light emitting diodes comprises a plurality of micro light emitting diodes, wherein the plurality of micro light emitting diodes includes flexible thin-film light emitting diodes, wherein the array of flexible light emitting diodes encircles the interior wall of the pipe, and wherein the array of flexible light emitting diodes comprises an array of spalled light emitting diodes.

2. The system of claim 1, further comprising:
a second array of photovoltaic cells coupled to an exterior surface of the storage reservoir.

3. The system of claim 1, further comprising:
a backup power source coupled to the first array of photovoltaic cells.

4. The system of claim 3, wherein the backup power source comprises a thin film battery integrated with at least one photovoltaic cell in the first array of photovoltaic cells.

5. The system of claim 3, wherein the backup power source comprises an external battery module connected to at least one photovoltaic cell in the first array of photovoltaic cells.

6. The system of claim 1, wherein the array of flexible light emitting diodes comprises a plurality of light emitting diodes of different types that collectively emit a range of wavelengths of germicidal radiation.

7. The system of claim 1, further comprising:
a sensor coupled to the pipe for detecting turbidity or obstructions.

8. The system of claim 1, further comprising:
a biosensor coupled to the storage reservoir for monitoring a level of disinfection of the sample of water.

9. The system of claim 1, wherein each light emitting diode of the array of spalled light emitting diodes is electrically coupled to other light emitting diodes of the array of spalled light emitting diodes via a system of interconnects.

10. A method for disinfecting a sample of fluent water, the method comprising:
generating a current using an array of photovoltaic cells, wherein the array of photovoltaic cells encircles an exterior wall of a pipe for transporting the sample, wherein the array of photovoltaic cells comprises a plurality of micro photovoltaic cells, wherein the plurality of micro photovoltaic cells includes flexible thin-film photovoltaic cells;
powering an array of flexible light emitting diodes applied directly to an interior wall of the pipe using the current that is generated, wherein the array of flexible light emitting diodes emits a germicidal wavelength of radiation, wherein the array of flexible light emitting diodes comprises a plurality of micro light emitting diodes, wherein the plurality of micro light emitting diodes includes flexible thin-film light emitting diodes, wherein the array of flexible light emitting diodes encircles the interior wall of the pipe, and wherein the array of flexible light emitting diodes comprises an array of spalled light emitting diodes; and
exposing the sample of fluent water to the radiation while transporting the sample of fluent water from a source to a storage reservoir via the pipe.

11. The method of claim 10, wherein the generating comprises:
exposing the array of photovoltaic cells to solar radiation, wherein the array of photovoltaic cells converts the solar radiation into the current.

12. The method of claim 11, wherein the generating further comprises:
storing the current by a backup power source; and
powering the array of flexible light emitting diodes using the backup power source.

13. The method of claim 10, wherein the exposing comprises:
adjusting a flow rate of the sample of fluent water to achieve a desired level of disinfection.

14. The method of claim 10, wherein the exposing comprises:
adjusting a diameter of the pipe used for the transporting to achieve a desired level of disinfection.

15. The method of claim 10, wherein the exposing comprises:
adjusting a length of the pipe used for the transporting to achieve a desired level of disinfection.

16. The method of claim 10, wherein the exposing comprises:
adjusting an intensity of light from the array of flexible light emitting diodes to achieve a desired level of disinfection.

17. The method of claim 10, wherein the exposing comprises:
adjusting a spacing between light emitting diodes in the array of flexible light emitting diodes to achieve a desired level of disinfection.

18. The method of claim 10, wherein each light emitting diode of the array of spalled light emitting diodes is electrically coupled to other light emitting diodes of the array of spalled light emitting diodes via a system of interconnects.

19. A system for disinfecting a sample of water, the system comprising:
a pipe having an inlet for engaging a source of the sample of water;
a storage reservoir connected to an outlet of the pipe for holding the sample of water;
a first array of photovoltaic cells coupled to an exterior wall of the pipe for converting solar radiation into a current; and
an array of flexible, spalled light emitting diodes coupled directly to an interior wall of the pipe and powered by the current, wherein the array of flexible, spalled light emitting diodes emits a germicidal wavelength of radiation.

20. The system of claim 19, wherein each light emitting diode of the array of flexible, spalled light emitting diodes is electrically coupled to other light emitting diodes of the array of flexible, spalled light emitting diodes via a system of interconnects.

* * * * *